United States Patent [19]

Tawara et al.

[11] 4,368,337
[45] Jan. 11, 1983

[54] PROCESS FOR CONVERTING GLYCOL DIALKYL ETHER

[75] Inventors: Kinya Tawara; Hiroki Kamiyama, both of Soka; Shigenori Nakashizu, Satte; Takashi Kaneko, Soka; Tadahiro Wakui, Soka; Tadashi Matsumoto, Soka, all of Japan

[73] Assignee: Maruzen Oil Co., Ltd., Osaka, Japan

[21] Appl. No.: 248,913

[22] Filed: Mar. 30, 1981

[30] Foreign Application Priority Data

Mar. 28, 1980 [JP] Japan .................................. 55/40645

[51] Int. Cl.³ .............................................. C07C 41/01
[52] U.S. Cl. .................................... 568/613; 568/622; 568/678; 568/679; 568/866; 568/907; 585/639
[58] Field of Search ............... 568/622, 613, 678, 679, 568/866, 907; 585/639

[56] References Cited

U.S. PATENT DOCUMENTS

| | | | |
|---|---|---|---|
| 3,121,124 | 2/1964 | Verdol | 585/639 |
| 3,840,606 | 10/1974 | Vanlerberghe | 568/680 |
| 4,254,290 | 3/1981 | Chambers | 568/866 |

FOREIGN PATENT DOCUMENTS 55-33422  3/1980  Japan .................................. 568/678

OTHER PUBLICATIONS

Evans et al., I & EC pp. 1186–1188, vol. 28, No. 10, 1936.
McCutcheon, Synthetic Detergents, MacNair-Dorland Co., New York, 1950, p. 273.
Burwell, Chem. Rev. 54, (1954) p. 629.

*Primary Examiner*—Howard T. Mars
*Attorney, Agent, or Firm*—Sughrue, Mion, Zinn, Macpeak & Seas

[57] ABSTRACT

A process is described for converting glycol dialkyl ether without substantial formation of olefin oligomers by reaction with water, comprising reacting a feed glycol di-tertiary alkyl ether represented by structural formula (A) with water using a strongly acidic cation-exchange resin as a catalyst and a reaction temperature of from 40° C. to 150° C. under a pressure of from 1 to 70 kg/cm² (absolute pressure) in a molar ratio of water/feed glycol di-tertiary alkyl ether represented by the structural formula (A) of from 0.05/1 to 60/1, to convert the ether of formula (A) into at least one of (1) glycol mono-tertiary alkyl ether represented by the structural formula (B) and tertiary alcohol represented by the structural formula (C), or (2) glycol mono-tertiary alkyl ether represented by the structural formula (B) tertiary alcohol represented by the structural formula (C) and tertiary olefin represented by the structural formula (D); wherein (A), (B), (C), and (D) are as follows:

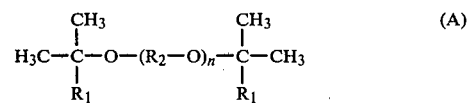

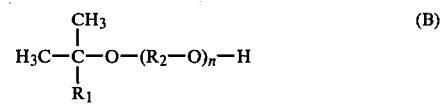

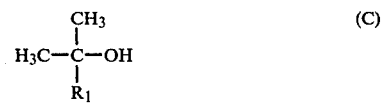

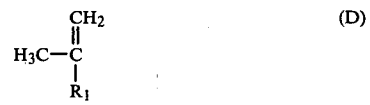

wherein $R_1$ represents a methyl group, an ethyl group, or a propyl group, n represents an integer of from 1 to 10, and $R_2$ represents an alkylene group having from 2 to 14 carbon atoms, and the total number of carbon atoms in the group $-(R_2-O)_n-$ is from 2 to 30.

13 Claims, No Drawings

PROCESS FOR CONVERTING GLYCOL DIALKYL ETHER

BACKGROUND OF THE INVENTION

The present invention relates to a process for converting glycol di-tertiary alkyl ether (referred to hereinafter as DAE), and particularly to a process for converting DAE into at least one of glycol mono-tertiary alkyl ether (referred to hereinafter as MAE) and tertiary alcohol, or tertiary olefin.

DAE is produced as a by-product when glycol mono-tertiary alkyl ether is produced by reacting glycol with tertiary olefin in the presence of an acid catalyst, as described, for example, in U.S. Pat. No. 3,317,483. Although MAE is useful as a solvent, a dispersing agent or a diluent, etc., in the industrial fields of coatings, inks, etc., DAE is of relatively little value. Accordingly, it would be very desirable if the DAE could be converted into more useful compounds such as glycol monoethers or alcohols. However, a process for converting DAE has not been known heretofore.

It has been known to obtain alcohols by reacting ethers such as dialkyl ether with water in a presence of sulfuric acid, hydrochloric acid, low molecular weight organic sulfonic acid (for example, benzenesulfonic acid, paratoluenesulfonic acid, sulfoacetic acid or sulfolauric acid), and fluoroacetic acid or chloroacetic acid, but when such a known process is applied to DAE, considerable amounts of oligomers of tertiary olefin, such as dimers or trimers of tertiary olefin, etc., are formed in addition to MAE, tertiary alcohol, and tertiary olefin (e.g., see Comparative Examples 1 and 2 hereinafter). In the case of industrially obtaining MAE and tertiary alcohol from the above described production mixture by means such as distillation, the presence of oligomers of tertiary olefin not only causes lowering of the yield of the desired product, but also requires a complicated separation means. Further, there is a problem in that the oligomers are present into the tertiary alcohol and/or MAE as impurities.

As processes for producing tertiary alcohol, a process which comprises sulfurizing tertiary olefin and hydrolyzing the product, and a process which comprises directly hydrating tertiary olefin have been known. However, they have a problem in that, since a mixed olefin fraction is necessarily used as the tertiary olefin feed, a part of the other olefins included in the mixed olefin fraction reacts to produce secondary alcohol as a by-product, as a result of which the desired tertiary alcohol is difficult to obtain in high purity.

SUMMARY OF THE INVENTION

The chief object of the present invention is to provide a process for converting DAE into more useful compounds, namely to provide a process for producing at least one of MAE and tertiary alcohol, and tertiary olefin, from DAE.

Another object of the present invention is to obtain tertiary alcohol having a high purity without forming secondary alcohols as a by-product in converting the DAE.

A further object of the present invention is to minimize formation of oligomers of tertiary olefins as a by-product in converting DAE.

Therefore, according to this invention, a process is provided for converting glycol dialkyl ether without substantial formation of olefin oligomers by reaction with water, comprising reacting a feed glycol di-tertiary alkyl ether represented by structural formula (A) with water using a strongly acidic cation exchange resin as a catalyst and a reaction temperature of from 40° C. to 150° C. under a pressure of from 1 to 70 kg/cm² (absolute pressure) in a molar ratio of water/feed glycol di-tertiary alkyl ether represented by the structural formula (A) of from 0.05/1 to 60/1, to convert the ether of formula (A) into at least one of (1) glycol mono-tertiary alkyl ether represented by the structural formula (B) and tertiary alcohol represented by the structural formula (C) and (2) tertiary olefin represented by the structural formula (D); wherein (A), (B), (C), and (D) are as follows:

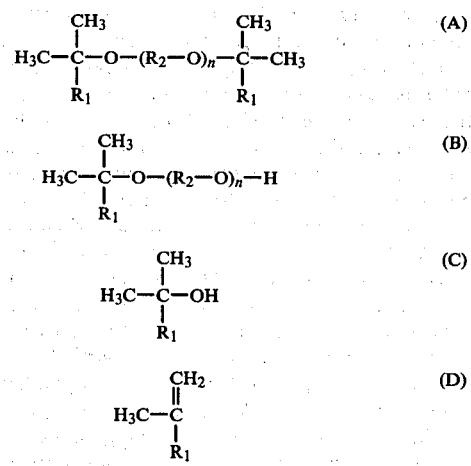

wherein $R_1$ represents a methyl group, an ethyl group, or a propyl group, n represents an integer of from 1 to 10, and $R_2$ represents an alkylene group having from 2 to 14 carbon atoms, and the total number of carbon atoms in the group $-(R_2-O)_n-$ is from 2 to 30.

DESCRIPTION OF THE PREFERRED EMBODIMENTS

As a result of extensive studies into the process for converting DAE, according to this invention, it has been found that in a process for converting DAE into at least one of (1) MAE and tertiary alcohol, and (2) tertiary olefin by decomposing DAE by reaction with water, MAE and tertiary alcohol and/or tertiary olefin are desirably formed, and formation of oligomers of tertiary olefin such as dimer or trimer of tertiary olefin, etc. as undesirable by-products reduced and tertiary alcohol having a high purity is obtained substantially without forming secondary alcohol as a by-product, when a strongly acidic cation exchange resin is used as a catalyst and the reacting condition specified above is selected.

The glycol di-tertiary alkyl ether (DAE) as a starting material in the process of the present invention is represented by structural formula (A). This glycol diether is decomposed by water in the presence of a strongly acidic cation-exchange resin to convert it into at least one of (1) the corresponding glycol mono-tertiary alkyl ether (MAE) represented by the structural formula (B) and tertiary alcohol represented by the structural formula (C), and (2) tertiary olefin represented by the structural formula (D). The reaction can be carried out while adding a glycol together with water to the reactants. In the case of carrying out the reaction in the presence of glycols, glycol di-tertiary alkyl ether represented by the structural formula (A) reacts with the glycols HO—$(R_2O)_n$—H (where $R_2$ and n each have the same meaning as described above) to form glycol mono-tertiary alkyl ether (MAE) represented by the structural formula (B). The reaction of DAE with the glycol progresses together with the reaction of DAE with water.

With respect to the DAE used as the starting material, $R_1$ in the above described formula represents a methyl group, an ethyl group, or a propyl group, $R_2$ represents an alkylene group having from 2 to 14 carbon atoms, and preferably from 2 to 8 carbon atoms, examples of which include ethylene, propylene, butylene, pentylene and hexylene groups, n represents an integer of from 1 to 10, and preferably an integer of from 1 to 3, and the total number of carbon atoms of the DAE is from 10 to 42, and preferably from 10 to 18. If the carbon atom number of the group —$(R_2$—O$)_n$— exceeds 30, the reaction rate of DAE is undesirably reduced. Examples of DAE include glycol di-tertiary butyl ethers such as ethylene glycol di-tertiary butyl ether, diethylene glycol di-tertiary butyl ether, triethylene glycol di-tertiary butyl ether, polyethylene glycol (n is 4 to 10) di-tertiary butyl ether, propylene glycol di-tertiary butyl ether, dipropylene glycol di-tertiary butyl ether, polypropylene glycol (n is 3 to 10) di-tertiary butyl ether or 1,4-butanediol di-tertiary butyl ether, glycol di-tertiary pentyl ethers such as ethylene glycol di-(1,1-dimethylpropyl)-ether, diethylene glycol di-(1,1-dimethylpropyl)ether or propylene glycol di-(1,1-dimethylpropyl)ether, glycol di-tertiary hexyl ethers such as ethylene glycol di-(1,1,2-trimethylpropyl)ether or ethylene glycol di-(1,1-dimethylbutyl)-ether, and glycol di-tertiary butyl ethers such as 2,3-butanediol di-tertiary butyl ether, hexylene glycol di-tertiary butyl ether or 1,12-dodecanediol di-tertiary butyl ether, etc.

Furthermore, as the glycol mono-tertiary alkyl ether (MAE) obtained from such DAE, there are corresponding mono-ethers, namely, glycol mono-tertiary butyl ethers such as ethylene glycol monotertiary butyl ether, diethylene glycol mono-tertiary butyl ether, triethylene glycol mono-tertiary butyl ether, polyethylene glycol mono-tertiary butyl ether, propylene glycol mono-tertiary butyl ether, dipropylene glycol mono-tertiary butyl ether, polypropylene glycol mono-tertiary butyl ether or 1,4-butanediol mono-tertiary butyl ether, glycol mono-tertiary pentyl ethers such as ethylene glycol mono-(1,1-dimethylpropyl)ether, diethylene glycol mono-(1,1-dimethylpropyl)ether or propylene glycol mono-(1,1-dimethylpropyl)ether, glycol mono-tertiary hexyl ethers such as ethylene glycol mono-(1,1,2-trimethylpropyl)ether or ethylene glycol mono-(1,1-dimethylbutyl)ether, and glycol mono-tertiary butyl ethers such as 2,3-butanediol mono-tertiary butyl ether, hexylene glycol mono-tertiary butyl ether or 1,12-dodecanediol mono-tertiary butyl ether, etc.

As the tertiary alcohol, there are corresponding alcohols, namely, tertiary butyl alcohol, 1,1-dimethylpropanol as tertiary pentyl alcohol, and tertiary hexyl alcohols such as 1,1,2-trimethylpropanol or 1,1-dimethylbutanol, etc.

As tertiary olefins (hydrocarbons having a double bond on the tertiary carbon atom, which are usually referred to as iso-olefins), there are the corresponding isobutylene, isoamylene, and isohexylene.

As the DAE used in the present invention, by-products obtained during the production of glycol mono-tertiary alkyl ether from glycol and tertiary olefin are a preferred source, but materials obtained by other reaction routes may also be used.

As the water for reaction with the DAE, though water which has a low metal ion content, such as water purified with ion-exchange resins or distilled water, etc., is preferred, any water may be used, provided that it does not contain a component which has an adverse influence upon the catalyst.

Examples of components having an adverse influence upon the catalyst include strong water-soluble inorganic acids, such as hydrochloric acid, sulfuric acid, etc.; strong water-soluble organic acids, such as paratoluenesulfonic acid, benzenesulfonic acid, etc.; and a substance capable of ion-exchange with a strongly acidic cation-exchange resin catalyst, e.g., inorganic cation such as $K^+$, $Mg^{2+}$, $Al^{2+}$, $Al^{3+}$, $Na^+$, $Ca^{2+}$, $Fe^{2+}$, $Fe^{2+}$, $Fe^{3+}$ and $Ni^{2+}$, or a substance of forming these cations in water (e.g., iron rust); organic bases such as primary amine, secondary amine, tertiary amine, amides, etc.; and ammonia. As the water used for reaction of this invention, the water containing none of the above-described components having an adverse influence upon the catalyst, or the water having a low content of these components, is desirably used.

In the case of carrying out the reaction while adding glycol together with water to the reaction system, examples of the glycol HO—$(R_2O)_n$—H ($R_2$ and n have each the same meaning as described above) include ethylene glycol, diethylene glycol, propylene glycol, polypropylene glycol, butanediol, hexylene glycol and 1,12-dodecanediol, etc.

By the addition of the glycol to the reaction system, the ratio of the MAE produced to the tertiary alcohol produced can be increased. Thus addition of the glycol into the reactants is useful for increasing the MAE produced and decreasing the tertiary alcohol produced, or adjusting the production ratio of MAE and tertiary alcohol to a desired level.

As the strongly acidic cation-exchange resin catalyst in the present invention, it is possible to use those which have sulfonic acid groups, such as styrene-sulfonic acid type cation-exchange resins (which are prepared by sulfonating copolymers of styrene and poly-unsaturated compound such as divinylbenzene, etc.), phenolsulfonic acid type cation-exchange resins (which are prepared by condensation of phenolsulfonic acid and formaldehyde), sulfonated coal, sulfonated asphalt and sulfonic acid type cation-exchange resins wherein sulfonic acid groups are bonded to a fluorine-contained resin (for example, Nafion produced by Du Pont Nemours, E. I.), etc. As the physical structure of these cation-exchange resins, both those of a gel type one and those of a macroporous type one can be used for this invention. A preferred total exchange capacity range of these strongly acidic cation exchange resins is at least about 0.5 meq/g-dry resin and particularly about 0.6-7.0 meq/g-dry resin. When the above described strongly acidic cation-exchange resins are used as a catalyst for the hydrolysis reaction of the DAE, dimers and trimers of tertiary olefin are not substantially formed, as compared with the cases of using sulfuric acid, low molecular weight sulfonic acid (for example, paratoluenesulfonic acid or benzenesulfonic acid, etc.), and chloroacetic acid or hydrochloric acid. Further, when the strongly acidic cation-exchange resins are used, there are advantages that products are easily separated, the apparatus corrodes less, and formation rate of tertiary alcohol is high.

In the process of the present invention the ratios of raw materials used, reaction temperature, and reaction pressure should be within the ranges specified above in the case of reacting DAE with water of with water and glycol, in addition to use of the strongly acidic cation-exchange resin as the catalyst. Namely, the molar ratio of water/DAE is from about 0.05/1 to 60/1, and preferably from about 0.5/1 to 30/1. If the amount of water is too small, oligomers of tertiary olefin form in considerable amounts. If the amount of water is too large, capacity of the apparatus must become excessively large. In the case of carrying out the reaction while adding glycol together with water, the molar ratio of water/DAE is in the above described range, namely, from about 0.05/1 to 60/1, and the molar ratio of DAE/glycol is from about 0.01/1 to 20/1, and preferably from about 0.05/1 to 10/1. If the amount of glycol is too low, the advantages caused by addition of glycol are lost. If it is too large, the capacity of the apparatus must become excessively large. The reaction temperature is from about 40° C. to 150° C., and preferably from about 50° C. to 120° C. If the reaction temperature is too low, the reaction rate becomes undesirably low. If it is too high, oligomers of tertiary olefin form in considerable amounts, and the catalyst is damaged by the heat. The reaction pressure is from about 1 to 70 kg/cm$^2$, and preferably from about 1 to 20 kg/cm$^2$. If the reaction pressure is too low, the reaction temperature is difficult to maintain at a desired value. If it is too high, the cost of apparatus becomes undesirably high. The amount of the catalyst is not especially limited. In a batch reaction process, however, it is preferred that the amount be from about 0.1% to 50% by weight, and more preferably from about 1% to 30% by weight, based on the total weight of the DAE and water raw materials. In a batch system or an agitation type batch system, it is preferred that the reaction time be from about 30 seconds to 50 hours, and more preferably from about 1 minute to 10 hours. In case of an agitation type continuous system, it is preferred that the resisdence time be from about 30 seconds to 50 hours, and more preferably from about 1 minute to 10 hours. In the case of a flow system, it is preferred that the liquid hourly space velocity be from about 0.05 to 20 hr$^{-1}$, and more preferably from about 0.1 to 10 hr$^{-1}$. Though the linear velocity is not limited especially, it is generally from about 20 cm/hr to 10 m/hr. Further, the reaction can be carried out in a gaseous phase, but it is preferred to carry it out in a liquid phase. In the case of carrying out the reaction while adding the glycol together with water to the reaction system, the reaction conditions except the molar ratio of DAE to the glycol can be the same as the reaction conditions in the case of carrying out the reaction with water without adding a glycol.

The reaction process can be carried out by a variety of techniques, for example, using a simple batch system, an agitation type batch system, an agitation type continuous system, fixed-bed continuous flow system, etc. However, the reaction is preferred to be carried out by the fixed-bed continuous flow system from the viewpoint of damaging the catalyst or separating it from the products.

In the batch system, the reaction is generally carried out without feeding raw materials (that is, the raw materials are all present initially). In the agitation type batch system and the agitation type continuous system, DAE or water, or DAE and water, may be added one after another to the reaction system as the reaction progresses. In the fixed-bed continuous flow system, the raw materials are fed from the top or the bottom of the reaction tower in either parallel flow or countercurrent flow. However, DAE or water, or DAE and water may also be fed to a middle position of the reaction tower.

Since DAE has a low solubility in water, the conversion is low, when DAE and water are subjected to reacting directly. Accordingly, in the present invention, the reaction may be carried out with adding a material which increases miscibility of DAE with water or solubility of DAE in water to the system, by which the reaction effectively proceeds and the desired product is rapidly obtained. Any material may be used, if it increases the miscibility of DAE with water. If if further preferred to select the material and to control an amount thereof so as not to result in division into a DAE phase and an aqueous phase, but the materials used may form two phases. As the material which increases the miscibility of DAE with water, example include polar solvents and surface active agents.

As suitable solvents which increase mutual solubility of DAE and water, examples include alcohols having from 1 to 30 carbon atoms, such as methanol, ethanol, propanol, butanol, hexanol or octanol, etc., glycol monoalkyl ethers such as ethylene glycol monomethyl ether, ethylene glycol monoethyl ether, ethylene glycol monobutyl ether, diethylene glycol monomethyl ether, diethylene glycol monoethyl ether or diethylene glycol monobutyl ether, etc., phenols such as phenol, or cresol, etc., ketones such as acetone, methyl ethyl ketone or methyl isobutyl ketone, etc., cyclic ethers such as tetrahydrofuran, dioxane, trioxane or tetrahydropyran, etc., esters such as methyl acetate, ethyl acetate, butyl acetate, methyl propionate, ethyl propionate, butyl propionate, or γ-butyrolactone, etc., formamides such as dimethylformamide or diethylformamide, etc., and sulfoxides such as dimethyl sulfoxide, diethyl sulfoxide or diphenyl sulfoxide, etc. Furthermore, tertiary alcohol and glycol mono-tertiary alkyl ether produced by the process of the present invention are capable of utilizing directly as polar solvents. Since the crude reaction product contains tertiary alcohol or glycol monoether, though amounts thereof depend on the reacting condition, a part of the crude reaction product is circulated into the reaction system, by which the object of the invention can be attained. Further, in case of using as the raw material DAE prepared as a by-product in production of glycol mono-tertiary alkyl ethers from tertiary olefin and glycol, the raw material can be used directly in a state that it contains monoethers and glycols. A part of the ethers is hydrolyzed during the reaction.

A suitable amount of the solvent used is from about 0.01 to 10 times the weight of the DAE.

As the surface active agents, nonionic surface active agents are preferably used. As examples of the nonionic surface active agents, there are those which contain a hydrophilic group derived from polyethylene glycols or polyhydric alcohols, etc. and a hydrophobic group derived from higher alcohols, alkylphenols, aliphatic acids, higher aliphatic amines, aliphatic amides or oils and fats, etc., and those having a larger hydrophilic property are suitably used. Examples of the nonionic surface active agents include polyoxyethylene oleyl ether, polyoxyethylene lauryl ether, polyoxyethylene stearyl ether, polyoxyethylene nonylphenol ether, polyoxyethylene octylphenol ether, polyoxyethylene monolaurate, polyoxyethylene monooleate, polyoxyethylene monostearate, polyoxyethylene sorbitan monolaurate, sorbitan monolaurate, polyoxyethylene sorbitan monostearate, polyoxyethylene sorbitan monooleate, oxyethylene oxypropylene block polymers, alkyl-alkylolamide, lauric acid diethanolamide, polyoxyethylene distearate and glycerol monostearate, etc. A suitable amount of the surface active agent is from about 0.1 to 30% by weight, and preferably from about 0.5–10% by weight, based on the weight of DAE.

Under the above described reacting condition, the DAE is hydrolyzed by reacting with water to form equimolar amounts of glycol mono-tertiary alkyl ether and tertiary alcohol, and the DAE, glycol mono-tertiary alkyl ether, and tertiary alcohol may be further decomposed to form tertiary olefin. Further, glycol mono-tertiary alkyl ether is partially converted into tertiary alcohol. In these reactions, glycols represented by the formula HO—$(R_2O)_n$—H (where $R_2$ and n have each the same meaning as described above), for example, ethylene glycol, diethylene glycol, propylene glycol, polypropylene glycol, butanediol, hexylene glycol and 1,12-dodecanediol, are formed. Accordingly, it is possible to change the production ratios of glycol mono-tertiary alkyl ether, tertiary alcohol and tertiary olefin by changing the reacting condition within the above described ranges. Namely, glycol mono-tertiary alkyl ether and tertiary alcohol are produced in relatively large amounts at a reaction temperature of from about 40° C. to 150° C. and a reaction pressure of from about 1 to 70 kg/cm$^2$ when the amount of water used is such that the molar ratio of water/DAE is from about 0.1/1 to 60/1. On the other hand, tertiary olefin can be produced in a relatively large amount when the reaction temperature is high, the reaction pressure is low, or the amount of water used is low, such as at a reaction temperature of from about 50° to 150° C., under a reaction pressure of from about 1 to 40 kg/cm$^2$, or at a molar ratio of water/DAE of from about 0.05/1 to 10/1.

In the case of carrying out the reaction in a presence of glycols in the reaction system, reactions of glycols with DAE progress, together with a hydrolysis reaction of DAE with water, to convert into glycol mono-tertiary alkyl ether represented by the structural formula (B).

Separation and purification of the resulting reaction mixture can be carried out by conventional separation processes, such as distillation, extraction, extractive distillation, azeotropic distillation, etc.

When DAE is subjected to reacting with water in the presence of the strongly acidic cation-exchange resin according to the present invention, DAE decomposes to form at least one of (1) glycol monoalkyl ether and tertiary alcohol, and (2) tertiary olefin, and oligomers of tertiary olefin such as dimers or trimers of tertiary olefin are not substantially formed. Accordingly, in case of obtaining glycol monoalkyl ether and tertiary alcohol from this product by means such as fractional distillation, etc., there are advantages in that separation is easily carried out and tertiary olefin and glycol are obtained in high purities, because oligomers of tertiary olefin are not substantially present.

Further, according to the invention, it is possible to convert DAE having a low utility value prepared as a by-product in production of, for example, glycol monotertiary alkyl ether into useful glycol mono-tertiary alkyl ether and tertiary alcohol. In the prior processes for producing tertiary alcohol, which comprised hydrating tertiary olefin to produce tertiary alcohol, it was necessary to use a step for separating the secondary alcohol in order to increase the purity of tertiary alcohol when a mixed olefin fraction is used as the tertiary olefin feed, because a part of other olefins contained therein reacts to produce the secondary alcohol as a by-product and the purity of tertiary alcohol was reduced.

On the contrary, in the process of this invention, the secondary alcohol is not produced as a by-product.

Further, in the prior processes for producing tertiary alcohol which comprised hydrating tertiary olefin, oligomers of tertiary olefin were produced in considerable amounts as by-products.

However, in the process of this invention, the oligomers of tertiary olefin are not substantially produced as by-products.

According to the process of this invention, tertiary olefin having a high purity can be produced if desired by selecting appropriate conditions. Moveover, the reaction according to this invention can be more effectively carried out by using suitable solvents or surface active agents as described above.

In the following, the present invention is illustrated in more detail with reference to examples.

EXAMPLES 1–3

A 300 ml autoclave equipped with a stirrer was charged with 12.1 g of a macroporous type strongly acidic cation-exchange resin (Amberlyst 15, produced by Rohm & Haas Co., total exchange capacity: 4.9 meq/g-dry resin), 50.4 g of ethylene glycol di-tertiary butyl ether and 25.2 g of water, and nitrogen gas was enclosed therein. The reaction was carried out at 75° C. for 2 hours in Example 1, at 75° C. for 6 hours in Example 2, and at 140° C. for 12 minutes in Example 3. The reaction pressure was 3.5 kg/cm$^2$ in Examples 1 and 2 and 14 kg/cm$^2$ in Example 3. When the reaction product was analyzed, the resulted mixture had a composition as shown in Table 1.

According to the results shown in Table 1, ethylene glycol di-tertiary butyl ether is converted into ethylene glycol mono-tertiary butyl ether and tertiary butyl alcohol, and isobutylene is formed, too. In Examples 1–3, formation of isobutylene oligomers such as diisobutylene, etc. was not observed at all, and the recovered isobutylene had a very high purity, as high as 99% by volume or more. The product did not contain n-butyl alcohol and secondary butyl alcohol, and tertiary butyl alcohol separated from the product by distillation had a very high purity.

TABLE 1

| Example | 1 | 2 | 3 |
|---|---|---|---|
| Reaction temperature (°C.) | 75 | 75 | 140 |
| Reaction time (hr) | 2 | 6 | 0.2 |
| Product (g) | | | |
| Isobutylene | 0.1 | 0.3 | 15.2 |
| Diisobutylene | 0 | 0 | 0 |
| DBE *1 | 40.1 | 31.6 | 5.1 |
| MBE *2 | 7.0 | 5.9 | 5.9 |
| TBA *3 | 4.2 | 11.9 | 14.8 |
| EG *4 | tr | 3.6 | 13.0 |
| Water | 24.2 | 22.3 | 21.6 |

TABLE 1-continued

| Example | 1 | 2 | 3 |
|---|---|---|---|
| DBE conversion (%) | 20.4 | 37.3 | 89.9 |

(Note)
*1 Ethylene glycol di-tertiary butyl ether
*2 Ethylene glycol mono-tertiary butyl ether
*3 Tertiary butyl alcohol
*4 Ethylene glycol

EXAMPLES 4–6

The same reactor as in Example 1 was charged with 50.4 g of ethylene glycol di-tertiary butyl ether and 25.2 g of water. Further, as a catalyst 10.1 g of a macroporous type strongly acidic cation-exchange resin(Amberlite 200H, produced by Rohm & Hass Co., total exchange capacity: 4.6 meq/g-dry resin), was added in Example 4, 30.0 g of a sulfonic acid type strongly acidic ion-exchange resin wherein sulfonic acid groups are bonded to a fluorine-contained resin (Nafion, produced by Du Pont, total exchange capacity: 1.0 meq/g-dry resin) was added in Example 5, and 14 g of a gel type strongly acidic cation-exchange resin (Dowex 50W-X 12, produced by Dow Chemical Co., total exchange capacity: meq/g-dry resin) was added in Example 6. The reaction was carried out at a temperature of 75° C. under a pressure of 3.4 kg/cm$^2$ for 2 hours, respectively. The composition of the reaction product was as shown in Table 2. Formation of isobutylene oligomers was not observed at all, and the recovered isobutylene had a very high purity, as high as 99% by volume or more.

TABLE 2

| Example | 4 | 5 | 6 |
|---|---|---|---|
| Reaction temperature (°C.) | 75 | 75 | 75 |
| Reaction time (hr) | 2 | 2 | 2 |
| Product (g) | | | |
| Isobutylene | 0.1 | 0.2 | 0.1 |
| Diisobutylene | 0 | 0 | 0 |
| DBE | 41.2 | 40.5 | 41.3 |
| MBE | 6.2 | 6.7 | 6.1 |
| TBA | 4.0 | 4.0 | 3.8 |
| EG | tr | tr | tr |
| Water | 24.2 | 24.2 | 24.3 |
| DBE conversion (%) | 18.3 | 19.6 | 18.1 |

EXAMPLES 7–9

The same reactor as in Example 1 was charged with 12.5 g of a macroporous type strongly acidic cation-exchange resin (Amberlyst 15) and 25.0 g of water, and 50.4 g of triethylene glycol di-tertiary butyl ether was added in Example 7, 50.4 g of propylene glycol di-tertiary butyl ether was added in Example 8 and 50.4 g of ethylene glycol di-(1,1-dimethylpropyl)ether was added in Example 9. The reaction was carried out at a temperature of 75° C. under a pressure of 3.5 kg/cm$^2$ hours. When the composition of the reaction products was analyzed, the product in Example 7 was a mixture consisting of 0.2 g of isobutylene, 41.7 g of triethylene glycol di-tertiary butyl ether, 6.8 of triethylene glycol mono-tertiary butyl ether, 2.2 g of tertiary butyl alcohol, a trace of triethylene glycol and 24.5 g of water, the product in Example 8 was a mixture consisting of 0.1 g of isobutylene, 43.2 g of propylene glycol di-tertiary butyl ether, 5.1 g of propylene glycol mono-tertiary butyl ether, 2.7 g of tertiary butyl alcohol, a trace of propylene glycol and 24.3 g of water, and the product in Example 9 was a mixture consisting of 0.3 of isopentene, 44.7 g of ethylene glycol di-tertiary pentyl ether, 3.8 g of ethylene glycol mono-tertiary pentyl ether, 2.0 g of tertiary pentyl alcohol, trace of ethylene glycol and 24.6 g of water. The conversion of glycol di-tertiary alkyl ether was 17.3%, 14.3%, and 11.3%, in Examples 7, 8 and 9, respectively.

The glycol diethers react with water to convert into glycol monoethers and corresponding tertiary alcohols, and corresponding tertiary olefins are formed. Formation of olefin oligomers was not observed and the recovered tertiary olefin had a purity of 99% by volume or more.

EXAMPLES 10–13

A 300 ml autoclave equipped with a stirrer was charged with 12.1 g of a macroporous type strongly acidic cation-exchange resin: Amberlyst 15, 30.2 g of ethylene glycol di-tertiary butyl ether and 15.0 g of water and 15.1 g of ethylene glycol mono-tertiary butyl ether as a solvent, and a nitrogen gas was enclosed therein. The reaction was carried out at 75° C. for 1 hour in Example 10, at 75° C. for 4 hours in Example 11, at 90° C. for 1 hour in Example 12 and at 90° C. for 4 hours in Example 13. The pressure was 3.3 kg/cm$^2$ in Examples 10 and 11 and 4.0 kg/cm$^2$ in Examples 12 and 13. At the starting time of the reaction, the aqueous phase and the glycol diether phase were separated to form two layers. When the reaction products were analyzed, the results obtained were as shown in Table 3. In Examples 10–13, the conversion rate of ethylene glycol di-tertiary butyl ether became high, as compared with the cases in Examples 1–3 wherein the solvent was not added.

TABLE 3

| Example | 10 | 11 | 12 | 13 |
|---|---|---|---|---|
| Reaction temperature (°C.) | 75 | 75 | 90 | 90 |
| Reaction time (hr) | 1 | 4 | 1 | 4 |
| Product (g) | | | | |
| Isobutylene | 0.1 | 0.1 | 0.1 | 0.3 |
| Diisobutylene | 0 | 0 | 0 | 0 |
| DBE | 24.9 | 14.4 | 17.3 | 2.9 |
| MBE | 8.1 | 9.7 | 8.5 | 7.0 |
| TBA | 8.8 | 16.7 | 14.9 | 28.0 |
| EG | 5.6 | 8.5 | 8.1 | 13.9 |
| Water | 12.9 | 10.9 | 11.4 | 8.2 |
| DBE conversion (%) | 17.5 | 52.3 | 42.7 | 90.4 |

EXAMPLE 14

A 300 ml autoclave equipped with a stirrer was charged with 12.1 g of a macroporous type strongly acidic cation-exchange resin (Amberlyst 15), 30.2 g of ethylene glycol di-tertiary butyl ether, 7.30 g of water and 31.6 g of ethylene glycol mono-tertiary butyl ether as a solvent, and a nitrogen gas was enclosed therein. The reaction was carried out at a temperature of 75° C. under a pressure of 3.5 kg/cm$^2$ for 1 hour. At the starting time of the reaction, separation of the aqueous phase and the ethylene glycol diether phase was not observed, i.e., the mixture consisted of one phase. When the reaction product was analyzed, it had a composition consisting of 0.1 g of isobutylene, 17.0 g of ethylene glycol di-tertiary butyl ether, 12.7 g of ethylene glycol mono-tertiary butyl alcohol, 22.9 g of tertiary butyl alcohol, 14.6 g of ethylene glycol and 1.8 g of water, and the conversion of ethylene glycol di-tertiary butyl ether was 43.7%. Formation of isobutylene oligomers was not observed, and the recovered isobutylene had a very high purity, as high as 99% by volume or more.

The conversion rate of ethylene glycol di-tertiary butyl ether is higher in this example wherein the reaction was carried out as a homogeneous phase than in Example 10 wherein two phases were separated at the starting time of the reaction.

EXAMPLES 15-18

The reaction was carried out by the same procedure as in Example 10 except that 15.1 g of tertiary butyl alcohol (Example 15), 15.1 g of ethylene glycol mono-n-butyl ether (Example 16), 15.1 g of methyl isobutyl ketone (Example 17) or 15.1 g of dioxane (Example 18) was added as the solvent instead of the ethylene glycol mono-tertiary butyl ether that was used as the solvent in Example 10. Results are shown in Table 4. The conversion rate of ethylene glycol di-tertiary butyl ether became high by carrying out the reaction in a presence of the solvent.

TABLE 4

| Example | 15 | 16 | 17 | 18 |
|---|---|---|---|---|
| Product (g) | | | | |
| Isobutylene | 0.1 | 0.1 | 0.1 | 0.1 |
| Diisobutylene | 0 | 0 | 0 | 0 |
| DBE | 25.0 | 24.6 | 26.3 | 24.1 |
| MBE | 3.5 | 3.8 | 2.6 | 4.1 |
| TBA | 17.2 | 2.2 | 1.6 | 2.5 |
| EG | tr | tr | tr | tr |
| Water | 14.5 | 14.5 | 14.6 | 14.4 |
| MnBE *1 | — | 15.1 | — | — |
| MIBK *2 | — | — | 15.1 | — |
| Dioxane | — | — | — | 15.1 |
| DBE conversion (%) | 17.2 | 18.5 | 12.9 | 20.2 |

(Note)
*1 Ethylene glycol mono-n-butyl ether
*2 Methyl isobutyl ketone

EXAMPLES 19 AND 20

The same autoclave as in Example 1 was charged with 12.1 g of a macroporous type strongly acidic cation-exchange resin (Amberlyst 15), 30.2 of ethylene glycol di-tertiary butyl ether and 15.0 g of water, and 3 g of a surface active agent (polyoxyethylene sorbitan monolaurate; under the trademark "Tween 20", value of hydrophilic-lipophilic balance (HLB): 16.7), and 3 g of a surface active agent (polyoxyethylene monostearate; Nissan nonion S-10, value of HLB:15.0) were added in Example 19 and Example 20, respectively. The reaction was carried out at 75° C. under 3.5 kg/cm² for 1 hour. Results are shown in Table 5.

TABLE 5

| Example | 19 | 20 |
|---|---|---|
| Product (g) | | |
| Isobutylene | 0.1 | 0.1 |
| Diisobutylene | 0 | 0 |
| DBE | 26.1 | 25.9 |
| MBE | 2.8 | 2.9 |
| TBA | 1.6 | 1.7 |
| EG | tr | tr |
| Water | 14.6 | 14.6 |
| Surface active agent | 3.0 | 3.0 |
| DBE conversion (%) | 13.6 | 14.2 |

EXAMPLE 21

A stainless steel reaction tube having a 12.7 mm inside diameter and 1 m in length was filled with a macroporous type strongly acidic cation-exchange resin (Amberlyst 15) and a mixture consisting of 20.2 parts by weight of ethylene glycol di-tertiary butyl ether, 25.3 parts by weight of ethylene glycol monotertiary butyl ether, 22.4 parts by weight of tertiary butyl alcohol, 12.5 parts by weight of ethylene glycol, 19.4 parts by weight of water and 0.1 parts by weight of isobutylene was passed therethrough at a flow rate of 23.7 g/hr to carry out the reaction. The reacting conditions were a 75° C. temperature, 10 kg/cm² of pressure, 0.21 hr⁻¹ liquid space velocity, and 21 cm/hr linear velocity. The reaction product had a composition consisting of 5.0 parts by weight of ethylene glycol di-tertiary butyl ether, 19.7 parts by weight of ethylene glycol mono-tertiary butyl ether, 38.7 parts by weight of tertiary butyl alcohol, 20.7 parts by weight of ethylene glycol, 15.0 parts by weight of water and 1.8 parts by weight of isobutylene, and the conversion of ethylene glycol di-tertiary butyl ether was 75.3%. Formation of isobutylene oligomers was not observed at all, and the recovered isobutylene had a high purity as high as 99% by volume or more.

EXAMPLE 22

The same reactor as in Example 1 was charged with 12.5 of Amberlyst 15, 25.0 g of water and 50.4 g of hexylene glycol di-(1,1-dimethylpropyl)ether, and the reaction was carried out at a temperature of 75° C. under a pressure of 3.3 kg/cm³ for 2 hours.

When the reaction product was analysed, the mixture consisted of 0.2 g of isopentene, 45.2 g of hexylene glycol di-(1,1-dimethylpropyl)ether, 3.8 g of hexylene glycol mono-(1,1-dimethylpropyl)ether, 1.5 g of tertiary pentyl alcohol, trace of hexylene glycol and 24.7 g of water. Formation of isopentene oligomers was not observed.

EXAMPLE 23

0.057 mols of DBE, 0.110 mols of water and 0.0565 mols of ethylene glycol were subjected to reacting in an autoclave at 75° C. for 2 hours. Results of analyzing a liquid product after separation of isobutylene are shown in the following table. The catalyst used was 5.2 g of Amberlyst 15. Formation of isobutylene oligomers was not observed.

TABLE 6

| Component | Raw material (mol) | Product (mol) |
|---|---|---|
| Ethylene glycol | 0.565 | 0.537 |
| Diisobutylene | 0 | 0 |
| DBE | 0.057 | 0.007 |
| MBE | 0 | 0.078 |
| Water | 0.110 | 0.092 |
| Tertiary butyl alcohol | 0 | 0.018 |

EXAMPLE 24

The same reactor as in Example 1 was charged with 50.4 g of 1,12-dodecanediol di-tertiary butyl ether, 25.2 g of water and 12.1 g of a macroporous type strongly acidic cation-exchange resin (Amberlyst 15) and the reaction was carried out at a temperature of 75° C. under a pressure of 3.0 kg/cm² for 4 hours.

The resulting product was a mixture consisting of 0.6 g of isobutylene, 43.2 g of 1,12-dodecanediol di-tertiary butyl ether, 5.9 g of 1,12-dodecanediol mono-tertiary butyl ether, 1.0 g of tertiary butyl alcohol, trace of 1,12-dodecanediol and 24.9 g of water.

The purity of the recovered isobutylene was 99% by volume or more. Isobutylene oligomers were not formed at all.

EXAMPLE 25

The same reactor as in Example 1 was charged with 50.4 g of polyethylene glycol di-tertiary butyl ether (average molecular weight: about 500; n: about 7-10), 25.2 g of water and 12.1 g of a macroporous type strongly acidic cation-exchange resin: Amberlyst 15 as the catalyst, and the reaction was carried out at a temperature of 75° C. under a pressure of 3.0 kg/cm² for 5 hours.

The resulting product was a mixture consisting of 0.1 g of isobutylene, 45.9 g of polyethylene glycol di-tertiary butyl ether, 4.1 g of polyethylene glycol mono-tertiary butyl ether, 0.4 g of tertiary butyl alcohol, a trace of polyethylene glycol, and 25.1 g of water.

The purity of the recovered isobutylene was 99% by volume or more. Isobutylene oligomers were not formed at all.

EXAMPLE 26

The same reactor as in Example 1 was charged with 25.0 g of ethylene glycol di-tertiary butyl ether, 13.0 g of water and 9 g of a strongly acidic cation-exchange resin (Amberlyst 15). Nitrogen gas was enclosed therein, and the reaction was carried out at 40° C. for 20 hours. The reaction pressure was 1.1 kg/m².

The resulting reaction product was a mixture consisting of 0.1 g of isobutylene, 23.8 g of ethylene glycol di-tertiary butyl ether, 0.6 g of ethylene glycol mono-tertiary butyl ether, 0.5 g of tertiary butyl alcohol, 0.1 g of ethylene glycol, and 12.9 g of water. Isobutylene oligomers were not formed at all.

EXAMPLE 27

A 300 ml 3-necked glass flask equipped with a stirrer and a refluxing tube was charged with 9.0 g of a macroporous type strongly acidic cation-exchange resin (Amberlyst 15), 69.7 g of ethylene glycol di-tertiary butyl ether and 0.5 g of water, and the reaction was carried out at 75° C. for 7 hours under atmospheric pressure.

The resulting reaction product was a mixture consisting of 11.4 g of isobutylene, 36.5 g of ethylene glycol di-tertiary butyl ether, 18.5 g of ethylene glycol mono-tertiary butyl ether, 1.6 g of tertiary butyl alcohol, 2.1 g of ethylene glycol and 0.1 g of water. Isobutylene oligomers were not formed at all.

Moreover, in the above described Examples 1-27, the reaction mixture did not contain secondary alcohol, and tertiary alcohols recovered from the reaction mixtures had a very high purity.

COMPARATIVE EXAMPLES 1 AND 2

The same reactor as in Example 1 was charged with 50.4 g of ethylene glycol di-tertiary butyl ether and 25.2 g of water. As a catalyst, 10 g of 96% sulfuric acid was added in Comparative Example 1 and 10 g of paratoluenesulfonic acid was added in Comparative Example 2. A nitrogen gas was enclosed therein, and the reaction was carried out at a temperature of 75° C. under a pressure of 3.5 kg/cm² for 1 hour.

When the products were analyzed, the results shown in Table 7 were obtained.

In Comparative Examples 1 and 2, the isobutylene oligomers such as diisobutylene and triisobutylene were formed as by-products in relatively large amounts. Further, the isobutylene, ethylene glycol mono-tertiary butyl ether, and tertiary butyl alcohol products which were respectively obtained by the distillation of the reaction products contained isobutylene oligomer as an impurity, and as a result, products having high purity were not obtained.

TABLE 7

| Comparative Example | 1 | 2 |
|---|---|---|
| Reaction temperature (°C.) | 75 | 75 |
| Reaction time (hr) | 1.0 | 1.0 |
| Product (g) | | |
| Isobutylene | 0.2 | 0.3 |
| Diisobutylene | 3.6 | 4.0 |
| Triisobutylene | 0.1 | Trace |
| DBE | 42.6 | 41.1 |
| MBE | 1.3 | 2.4 |
| TBA | 0.8 | 0.5 |
| EG | 2.3 | 2.5 |
| Water | 24.7 | 24.8 |
| DBE conversion (%) | 15.5 | 18.5 |

While the invention has been described in detail and with reference to specific embodiments thereof, it will be apparent to one skilled in the art that various changes and modifications can be made therein without departing from the spirit and scope thereof.

What is claimed is:

1. A process for converting glycol dialkyl ether without substantial formation of olefin oligomers by reaction with water, comprising reacting a feed glycol di-tertiary alkyl ether represented by structural formula (A) with water using a strongly acidic cation-exchange resin as a catalyst and a reaction temperature of from 40° C. to 150° C. under a pressure of from 1 to 70 kg/cm² (absolute pressure) in a molar ratio of water/feed glycol di-tertiary alkyl ether represented by the structural formula (A) of from 0.05/1 to 60/1, to convert the ether of formula (A) into (1) glycol mono-tertiary alkyl ether represented by the structural formula (B) and tertiary alcohol represented by the structural formula (C) or (2) glycol mono-tertiary alkyl ether represented by the structural formula (B), tertiary alcohol represented by the structural formula (C) and tertiary olefin represented by the structural formula (D); wherein (A), (B), (C), and (D) are as follows:

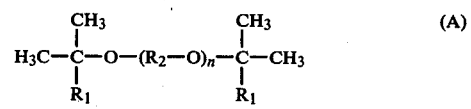

(A)

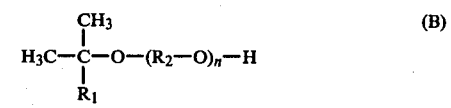

(B)

(C)

(D)

wherein $R_1$ represents a methyl group, and ethyl group, or a propyl group, n represents an integer of from 1 to 10, and $R_2$ represents an alkylene group having from 2 to 14 carbon atoms, and the total number of carbon atoms in the group $-(R_2-O)_n$ is from 2 to 30.

2. A process according to claim 1, in which the reaction is carried out in the presence of a polar solvent.

3. A process according to claim 2, in which the polar solvent is glycol monoalkyl ether.

4. A process according to claim 2, in which the polar solvent is an alcohol.

5. A process according to claim 1, in which the reaction is carried out in the presence of a surface active agent.

6. A process according to claim 1, 2, 3, 4 or 5, in which the feed glycol di-tertiary alkyl ether is ethylene glycol di-tertiary butyl ether, and the glycol mono-tertiary alkyl ether, the tertiary alcohol, and the tertiary olefin products are ethylene glycol mono-tertiary butyl ether, tertiary butyl alcohol, and isobutylene, respectively.

7. A process according to claim 1, 2, 3, 4, or 5, in which the feed glycol di-tertiary alkyl ether is diethylene glycol di-tertiary butyl ether, and the glycol mono-tertiary alkyl ether, the tertiary alcohol, and the tertiary olefin products are diethylene glycol mono-tertiary butyl ether, tertiary butyl alcohol, and isobutylene, respectively.

8. A process according to claim, 1, 2, 3, 4, or 5, in which the feed glycol di-tertiary alkyl ether is ethylene glycol di-tertiary pentyl ether, and the glycol mono-tertiary alkyl ether, and tertiary alcohol, and the tertiary olefin products are ethylene glycol mono-tertiary pentyl ether, tertiary pentyl alcohol, and isoamylene, respectively.

9. A process according to claim 1, 2, 3, 4, or 5, in which the feed glycol di-tertiary alkyl ether is ethylene glycol di-tertiary hexyl ether, and the glycol mono-tertiary alkyl ether, the tertiary alcohol, and the tertiary olefin products are ethylene glycol mono-tertiary hexyl ether, tertiary hexyl alcohol, and isohexene, respectively.

10. A process according of claim 1, 2, 3, 4, or 5, in which the reaction is carried out at a temperature of from 50° C. to 120° C., a pressure of from 1 to 20 kg/cm² (absolute pressure), and a molar ratio of water/feed glycol di-tertiary alkyl ether of from 0.5/1 to 30/1.

11. A process according to claim 1, in which the reaction is carried out using a batch system.

12. A process according to claim 1, in which the reaction is carried out using a fixed-bed continuous flow system.

13. A process according to claim 1, 2, 3, 4, or 5, wherein n represents and integer of from 1 to 3, and $R_2$ represents an alkylene group having from 2 to 8 carbon atoms.

* * * * *